United States Patent [19]

Keck et al.

[11] 4,330,462
[45] May 18, 1982

[54] STABILIZED POLYESTER COMPOSITION

[75] Inventors: Max H. Keck, Cuyahoga Falls;
Richard E. Gloth, Copley; James J. Tazuma, Stow, all of Ohio

[73] Assignee: The Goodyear Tire & Rubber Company, Akron, Ohio

[21] Appl. No.: 148,062

[22] Filed: May 12, 1980

[51] Int. Cl.³ ............................................. C08K 5/36
[52] U.S. Cl. .................................. 524/331; 568/47; 568/52; 568/54; 524/605; 524/739
[58] Field of Search ................................. 260/45.95 C

[56] References Cited

U.S. PATENT DOCUMENTS

| | | | |
|---|---|---|---|
| 3,330,804 | 11/1967 | O'Shea | 260/45.95 C |
| 3,637,863 | 1/1972 | Braus et al. | 260/45.95 C |
| 3,704,327 | 11/1972 | Neuworth | 260/45.95 C |
| 3,751,483 | 8/1973 | Cisney | 260/45.95 C |
| 4,104,255 | 8/1978 | Wollensak et al. | 260/45.95 C |
| 4,128,530 | 12/1978 | Cottman | 260/45.95 C |

*Primary Examiner*—V. P. Hoke
*Attorney, Agent, or Firm*—D. O. Nickey

[57] ABSTRACT

There is disclosed a method for the stabilization of polyester resins by incorporating in the resins certain types of 4-mercaptophenol derivatives.

10 Claims, No Drawings

STABILIZED POLYESTER COMPOSITION

TECHNICAL FIELD

The invention concerns stabilization of polyester resins by incorporating in the resins certain types of 4-mercaptophenol derivatives. The application particularly relates to the process of stabilizing polyester resins and to the compositions stabilized against thermal degradation and discoloration by the addition of compounds such as Bis-α,α'(4-hydroxyphenylthio)-1,4-diisopropylbenzene.

BACKGROUND ART

This invention relates to an improvement in saturated, linear polyester resins and to a method for preparing such resins having improved stability.

Highly polymeric polyester resins are derived from glycols and dicarboxylic acids or ester-forming derivatives thereof by esterification or ester exchange and subsequent polycondensation. In conducting the polycondensation reaction the reactants are subjected to prolonged conditions of elevated temperatures which can produce resin products having undesirable yellow or brown coloration. This undesirable coloration is carried over to the finished product made from these resins.

In addition to the development of color, polyesters degrade on exposure to heat and to conditions that favor hydrolysis of ester compounds. It is therefore desirable to provide polyester resins with stabilization against discoloration and degradation.

Various stabilizers for synthetic polymeric materials including polyesters have been proposed. However, only a very few of them are in actual commercial use in polyester because these stabilizers are required not only to exhibit superior stabilizing effects, but also to maintain the stabilizing effects for prolonged periods of time, have good reproducibility of the stabilization effects, not affect the physical properties of the resin adversely nor to color the resin, and also be easy to produce and be available at low cost.

Previously, dialkylhydroxyphenylalkanoic acid esters of di-and tri-pentaerythritol were proposed as stabilizers for polyesters and other organic materials (U.S. Pat. No. 3,642,868).

Compounds having a hindered phenol group or an analogous group are known as stabilizers for polymers, for example U.S. Pat. No. 3,644,482, German Offenlegungschrift No. 2,150,325, 2,158,014 and 2,158,015. Furthermore, U.S. Pat. No. 3,681,431, Dutch Laid-Open Publication No. 72.09214 and Dutch Laid-Open Publication No. 72.09230 propose compounds having a hindered phenol group.

U.S. Pat. No. 3,773,723 discloses a resin stabilized against discoloration by the addition of effective amounts of dialkyl thiodipropionates.

Hindered phenolic phosphorus compounds are suggested as polyester stabilizers in U.S. Pat. No. 3,386,952 and U.S. Pat. No. 3,676,393 suggests use of phosphonates as stabilizers while Canadian Pat. No. 973,994 discloses hindered phenolic phosphite compounds.

Synergistic stabilizing combinations are disclosed in U.S. Pat. No. 3,985,705 and U.S. Pat. No. 3,987,004 while U.S. Pat. No. 3,691,131 relates to phenolic antioxidants in combination with metal hypophosphites as stabilizers and U.S. Pat. No. 3,658,705 teaches use of a halogen compound, either alone or in combination with a copper compound as a stabilizer.

U.S. Pat. No. 3,300,440 relates to thiophosphate compounds as stabilizers for polyester resins. U.S. Pat. No. 3,640,948 discloses a sulfur-containing phenol having the formula OH—φ—S—R wherein φ represents a benzene ring, the hydroxyl group positioned para or ortho to the sulfur atom and R is alkyl, aryl or phenol. U.S. Pat. No. 3,640,948 does not disclose, suggest or claim that R can be selected from the group consisting of aralkyl radicals, polycyclic radicals, bis aralkyl or bis polycyclic radicals. In addition, U.S. Pat. No. 3,640,948 does not suggest or disclose bis-sulfide products as stabilizers for polyesters.

Although the above-identified patents directed to stabilize polyesters are of major interest, certain of the proposed polyester modifiers are known to be highly toxic and/or hazardous to use on commercial scale. Moreover, it has been found that these known compounds and processes do not completely solve or mitigate the long-standing problem of producing high molecular weight polyester stabilized against deterioration and discoloration under high temperature operating conditions. Accordingly, we have carried out considerable research in this field to find 4-mercaptophenol derivatives not disclosed or suggested by the prior art to be highly effective stabilizers for polyesters.

DISCLOSURE OF INVENTION

The present invention relates to an improved high molecular weight heat stable polyester and to a process for preparing it. The invention further provides a polyester resin which has excellent resistance to thermal and hydrolytic degradation and color stability.

It has been discovered that an improved heat and color stable polyester resin is obtained by incorporating therein a stabilizing amount of a phenolic stabilizer selected from at least one of the following generic formulae (I), (II) and (III):

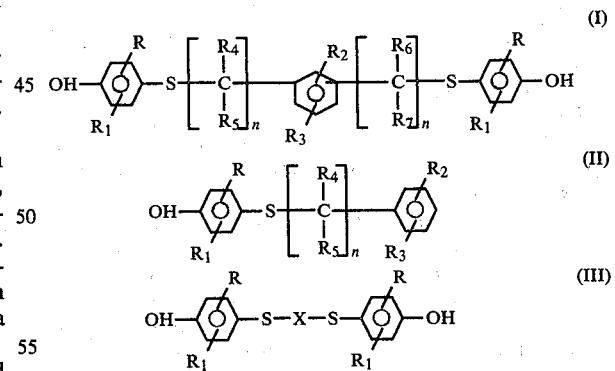

wherein R, $R_1$, $R_2$ and $R_3$ are the same or different radicals selected from the group consisting of hydrogen radical, alkyl radical of 1 to 18 carbon atoms, aralkyl radical of 7 to 24 carbon atoms; $R_4$, $R_5$, $R_6$ and $R_7$ are the same or different radicals selected from the group consisting of hydrogen radical, or alkyl radicals of 1 to 8 carbon atoms and n is 1 or 2; and X is selected from the group consisting of alkylene radicals of 2 to 18 carbon atoms, divalent cyclic radicals of 5 to 25 carbon atoms, divalent polycyclic radicals of 7 to 25 carbon atoms.

The phenolic stabilizers of formulae (I), (II) and (III) are illustrated by, but not limited to the following compounds:

Bis$\alpha,\alpha'$-(3,5-t-butyl-4-hydroxyphenylthio)-1,4-diisopropylbenzene,
Bis$\alpha,\alpha'$-(4-hydroxyphenylthio)-1,4-diisopropylbenzene,
$\alpha$-(4-hydroxyphenylthio)-$\alpha'$-(3,5-di-t-butyl-4-hydroxyphenylthio)-1,3-diisopropylbenzene,
$\alpha$-(3,5-di-t-butyl-4-hydroxyphenylthio)-$\alpha'$-(3-t-butyl-5-phenethyl-4-hydroxyphenylthio)-1,4-diisopropylbenzene,
Bis-$\alpha,\alpha'$-(3-isopropyl-5-t-butyl-4-hydroxyphenylthio)-1,4-di-sec-butylbenzene,
2-(1-phenethyl)-4(1-phenethyl-1-thio)phenol,
2,6-bis-(1-phenethyl)-4-(1-phenethyl-1-thio)phenol,
1,4-bis[1-(4-hydroxyphenylthio)ethyl]benzene, 1,6-bis-(3,5-di-t-butyl-4-hydroxyphenylthio)hexane,
5,11(12)-(4-hydroxyphenylthio)pentacyclo[8.2.4,7$0^{2,9}0^{3,8}$]-tetradecane,
5,11(12)-3,5-ditertiarybutyl-(4-hydroxyphenylthio)pentacyclo[8.2.1.$^{4,7}0^{2,9}0^{3,8}$]-tetradecane.

Another embodiment of the invention is a process for the preparation of a stabilized polyester wherein terephthalic acid is reacted with a glycol under esterification conditions and the resulting esterification product is polycondensed and a phenolic stabilizer is added, the improvement is characterized by the addition of the phenolic stabilizer when the polyester intrinsic viscosity is at least 0.5, said phenolic stabilizer is at least one selected from the group consisting of formulae (I), (II) and (III) wherein R, $R_1$ through $R_7$, and X are defined as above.

BEST MODE FOR CARRYING OUT THE INVENTION

The following examples illustrate the preparation of the stabilizers of the present invention.

EXAMPLE I

Preparation of bis$\alpha,\alpha'$-(4-hydroxyphenylthio)-1,4-diisopropylbenzene

A solution of 39.87 grams (0.316 mole) of 4-mercaptophenol and 1.12 milliliters (1.25 grams=0.5 gram $BF_3$=1.25 weight percent of 4-mercaptophenol) $BF_3Et_2O$ in 100 milliliters of toluene was stirred at 25° C. A solution of 25.0 grams (0.158) mole of 1,4-diisopropenylbenzene in 100 milliliters of toluene was added to the stirred solution over 43 minutes. Stirring and heating were continued for a total time of one hour. One hundred milliliters of water was then added as the mixture was stirred to deactivate the catalyst and remove the orange color. The white crystals were filtered, washed with toluene, and dried at 80° C., one millimeter pressure to yield 45.86 grams with a melting point of 158°–159° C. The yield of bis-$\alpha,\alpha'$-(4-hydroxyphenylthio)-1,4-diisopropylbenzene was 92.6 percent.

EXAMPLE II

Preparation of 2,6-bis-(1-phenethyl)-4-(1-phenethyl-1-thio)phenol

Sixty-three grams (0.5 mole) of 4-mercaptophenol and 3.5 grams of toluenesulfonic acid were heated to 60° C. Fifty-two grams (0.5 mole) of styrene was then added over 15 minutes. The reaction mixture was heated to 85° C. and 104 grams (1 mole) of styrene was added over 85 minutes. Stirring was continued for one hour before neutralizing the reaction mixture with a solution of 5 grams of sodium carbonate in 50 milliliters of water. The mixture was then stripped at 175° C., 25 mm Hg, to leave 219 grams of a moderately viscous product containing 7.11% sulfur. Theoretical sulfur for 2,6-bis-(1-phenethyl)-4-(1-phenethyl-1-thio)phenol is 7.3%.

EXAMPLE III

Preparation of 2,5 and/or 2,6-bis(4-hydroxyphenylthio)bicyclo[2.2.1]heptane

Sixty-six grams of 4-mercaptophenol, 100 ml. of toluene and 24.1 grams of 2,5-norbornadiene was heated to 70° C. and reacted 2.5 hours. After standing at room temperature for 16 hours, a white solid was filtered and washed with benzene-% sulfur, 17.9. Theoretical sulfur for 2,5 and/or 2,6-bis(4-hydroxyphenylthio)bicyclo[2.2.1]heptane is 18.0%. Melting point: 142°–146° C.

The resins which can be stabilized by the phenolic stabilizers of the present invention are described in U.S. Pat. No. 3,386,952 at column 4, lines 9–48, which is incorporated herein by reference. U.S. Pat. Nos. 3,535,286 and 3,542,737 also describe resins which can benefit by the practice of the present invention.

The reactions by which the resins are prepared are in general carried out in accordance with the usual known techniques. Thus, the resins are prepared from dicarboxylic acids and glycols or ester-forming derivatives thereof, generally by the ester interchange reaction of a lower alkyl ester of the acid with a glycol to form the glycol esters which are polymerized by condensation, with elimination of glycol to form high molecular weight resin. The reactions are preferably carried out in the absence of oxygen, generally in an atmosphere of inert gas such as nitrogen or the like, in order to lessen darkening and to make it possible to prepare a high molecular weight, lightly colored or colorless product. The condensation reaction is carried out under reduced pressure, generally below 10 millimeters of mercury pressure, and usually at or below one millimeter of mercury pressure, at a temperature in the range of from about 260° to 290° C. to form high molecular weight polyester having an intrinsic viscosity of at least 0.5 and generally at least 0.6 measured in a 60/40 phenol-tetrachloroethane mixed solvent at 30.0° C.

With polyesters made by the ester exchange route, (for example, dimethyl terephthalate plus ethylene glycol) phenolic stabilizers of structural formulae (I), (II) and (III) can be added to stabilize the polyester at any convenient time after the evolution of methanol has essentially ended. However, with polymers made by the direct reaction of reactants in the condensation stage the stabilizer should not be added until the molecular weight is relatively high, i.e., when it has an intrinsic viscosity of at least about 0.5 measured in a 60/40 phenol/tetrachloroethane mixed solvent at 30° C. at a concentration of approximately 0.4 grams of polymer per 100 cubic centimeters of solution. This is because the phenolic compounds may decompose under the acidic conditions which exist in the presence of a relatively large amount of carboxyl groups. It is therefore advisable that the condensation reaction has proceeded to such an extent that the greater portion of terephthalic acid has reacted with ethylene glycol, thus assuring a relatively low carboxyl group concentration. A convenient time of addition can be just prior to the discharge of the polymer batch from the polymerization reactor.

The phenolic compounds of this invention can also be added to the polyester resin after the polyester has been totally formed and has been removed from the reactor, for example, in an extruder or mixing device just prior to processing the resin into a film, fiber, molded product, etc. The preferred time of addition, however, is while the polymer is still in the polymerization reactor, since a more homogeneous mix can normally be accomplished at that time.

The amount of the stabilizer used can be varied over a wide range of concentrations. Generally the amount used will be from about 0.01 to 2.0 percent by weight of the polyester resin used. The preferred amounts usable will be in the range of from about 0.05 to 1.0 percent by weight of the polyester resin to obtain optimum stability in the resin. While a phenolic stabilizer of this invention will usually be used as the sole stabilizing agent in the polyester resin, it can be used in conjunction with other stabilizing agents such as triphenyl phosphite, or other phenolic stabilizers of this invention, if desired. If desired, pigments such as titanium dioxide, silicas, calcium carbonate, and carbon may also be incorporated into the polyester being stabilized.

The following examples illustrate the use of the phenolic stabilizers in the stabilization of polyethylene terephthalate (PET). They are not intended to be limiting.

of methanol ceased. To this reaction mixture was then added 0.075 gram of bis-$\alpha,\alpha'$-(4-hydroxyphenylthio)-1,4-diisopropylbenzene and the equivalent of 0.04 parts per thousand, by weight of the polymer, of a stock solution of triethylene diphosphite [P(TEDP)]. The reaction temperature was raised from 200° to 250° C. over a one hour period. After 15 minutes at 250° C. the pressure on the system was gradually reduced over a 20 minute period to 0.3 Torr at which point the reaction temperature was further increased to 275° C. After 90 minutes at 275° C. and 0.3 Torr the polyester exhibited a high melt viscosity and the polycondensation reaction was terminated. The intrinsic viscosity of this polymer was 0.537 and the color of the polymer was unusually white.

EXAMPLES V AND VI

In a manner similar to that described in Example IV two other polyesters were prepared, one of which contained Irganox 1010, (Tetrakis[methylene-3(3'-di-t-butyl-4'-hydroxyphenyl)propionate]methane) a commercially available stabilizer, and the other polymer contained no phenolic type stabilizer (Example VI). Samples of ground vacuum dried polyesters from Examples IV, V and VI were placed in a circulating air oven at 250° C. and were heated for 1, 2½ and 5 hours in order to compare thermal stability behavior. Table I below contains all pertinent data.

TABLE I

| Hours at 250° C. | Polymer from Example IV (0.15 wt.% Mercaptophenol derivative) | Polymer from Example V (0.15 wt.% Irganox 1010)* | Polymer from Example VI Control Polymer No Phenolic Stabilizer |
|---|---|---|---|
| 0 | I.V. ①= 0.537 Color = White | I.V. = 0.552 Color = White | I.V. = 0.572 Color = White |
| 1 | I.V. = 0.768 Color = White | I.V. = 0.793 Color = Light Brown | I.V. = 0.193 Color = Brown |
| 2½ | I.V. = 0.795 Color = White | I.V. = ② Color = Light Brown | I.V. = 0.155 Color = Brown |
| 5 | I.V. = 0.720 Color = Off-White | I.V. = 0.320 Color = Brown | I.V. = 0.141 Color = Dark Brown |

*Irganox 1010 has the structure:

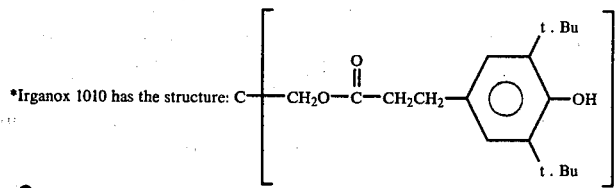

①Intrinsic Viscosity measured in a 60/40 phenol/tetrachloroethane mixed solvent at 30° C. at a concentration of approximately 0.4 grams of polymer per 100 cm³ of solution.
②I.V. could not be determined on this sample due to insolubles formed by crosslinking. On further heating it decomposed.

Unless otherwise indicated all parts are by weight.

In Examples IV through IX polyethylene terephthalate was prepared by the ester interchange method using dimethyl terephthalate (DMT) and ethylene glycol (EG) with a manganese acetate/antimony oxide catalyst system.

EXAMPLE IV

Use of bis-$\alpha,\alpha'$-(4-hydroxyphenylthio)-1,4-diisopropylbenzene and Triethylene Diphosphite A mixture of 50.44 grams of dimethyl terephthalate, 37.2 milliliters of ethylene glycol, 0.0152 gram of manganese acetate and 0.0152 gram of antimony trioxide was placed in a glass reactor tube equipped with a stirrer and a side arm with a condenser in distillation position. This mixture was heated in a nitrogen atmosphere at 200° C. for about 3 hours at which point the evolution

EXAMPLE VII

In a manner similar to that described in Example IV a polyester was prepared in which the phenolic stabilizer was 2,6-bis-(1-phenethyl)-4(1-phenethyl-1-thio)-phenol. The intrinsic viscosity of this polymer was 0.571.

EXAMPLE VIII

In a manner similar to that described in Example IV a polyester was prepared in which the phenolic stabilizer was 2-(1-phenethyl)-4-(1-phenethyl-1-thio)phenol. The intrinsic viscosity of this polymer was 0.544.

EXAMPLE IX

In a manner similar to that described in Example IV a polyester was prepared in which the phenolic stabilizer was 5,11(12)-(4-hydroxyphenylthio)pentacyclo[8.2.1$^{4,7}$0$^{2,9}$0$^{3,8}$]-tetradecane. The intrinsic viscosity of this polymer was 0.549.

EXAMPLE X

In a manner similar to that described in Example IV a polyester was prepared in which the phenolic stabilizer was 1,6-bis(3,5-di-tertiarybutyl-4-hydroxyphenylthio)hexane. The intrinsic viscosity of this polymer was 0.576.

EXAMPLE XI

In a manner similar to that described in Example IV a polyester was prepared in which the phenolic stabilizer was 1,4-bis[1-(4-hydroxyphenylthio)ethyl]benzene. The intrinsic viscosity of this polymer was 0.525.

Samples of polyesters taken from Examples VII—XI were ground to a powder, vacuum dried at 125° C. for 4 hours and then placed in a circulating air oven at 250° C. Samples were removed from the oven after 1, 2½ and 5 hours in order to compare changes in molecular weight (intrinsic viscosity) and changes in color. Data is presented in Table II.

of these stabilizers with polyester made by the direct esterification of terephthalic acid and ethylene glycol can be illustrated as follows.

A low molecular weight masterbatch of polyethylene terephthalate was prepared by reacting terephthalic acid and ethylene glycol under about 35 pounds of pressure and at about 250° to 270° C. This low molecular weight polyester contained 0.015 parts per thousand of sodium acetate and no antimony catalyst. Portions of this polyester were then used in the following examples.

EXAMPLE XII

A 50.44 gram quantity of the masterbatch polyester was mixed with 0.0152 gram of antimony trioxide in a glass reaction tube equipped with a stirrer and a side arm with a condenser in distillation position. This mixture was heated for one hour at 275° C. and at full vacuum (0.30 Torr). The reactor system was then restored to atmospheric pressure with nitrogen and a small sample of polymer melt was quickly removed for an intrinsic viscosity determination. To the melted polymer was added 0.02 parts per thousand of phosphorus in the form of triethylene diphosphite [P(TEDP)] and 0.075

TABLE II

| Polymer From Example No: | Phenolic Stabilizer | Polymer Color After 5 hrs.@250° C. | Intrinsic Viscosities Hours in Air at 250° C. | | | |
|---|---|---|---|---|---|---|
| | | | 0 | 1 | 2½ | 5 |
| VII | 2,6-Bis-(1-phenethyl)-4-(1-phenethyl-1-thio)phenol | Good | .574 | .666 | .732 | .738 |
| VIII | 2-(1-phenethyl)-4-(1-phenethyl)-1-thio)phenol | Very Good | .544 | .676 | .721 | .734 |
| IX | 5,11(12)-4-hydroxyphenylthio)pentacyclo[8.2.1.$^{4,7}$0.$^{2,9}$0.$^{3,8}$]tetradecane | Very Good | .540 | .607 | .651 | .676 |
| X | 1,6-Bis-(3,5-ditertiarybutyl-4-hydroxyphenylthio)hexane | Very Good | .574 | .674 | .715 | .710 |
| XI | 1,4-Bis-[4-hydroxyphenylthio)ethyl]-benzene | Good | .555 | .617 | .682 | .712 |

As indicated by the above data, the absence of a phenolic stabilizer (Polymer from Example VI) results in both poor color and reduced molecular weight on aging. Where a prior art stabilizer was used (No. V) although the molecular weight was preserved on aging, the color was very poor. The rest of the compositions which contained stabilizers of the present invention not only maintained molecular weight, but provided good color characteristics.

Examples VII–XI have illustrated the use of the phenolic stabilizers of the present invention with polyesters prepared by the dimethyl terephthalate route. The use gram of bisα,α'-(4-hydroxyphenylthio)-1,4-diisopropylbenzene. The pressure in the reactor was again reduced to 0.3 Torr and the mixture was stirred and heated at 275° C. for 35 minutes at which point a high melt viscosity had been attained and the reactor was shut down. The final intrinsic viscosity was found to be 0.618 and the intrinsic viscosity of the sample taken just prior to the addition of the stabilizer was found to be 0.356.

The examples which are listed in Table III were prepared in a manner similar to that described in Example XII. Example XII–XXII utilize different stabilizers and different concentrations of P(TEDP).

TABLE III

| Example | P(TEDP) [Parts Per Thousand] | Antioxidant Stabilizer | I.V. at Addition of Stabilizer | Visual Color[a] Rating - 5 hrs at 250° C. | Intrinsic Viscosity Hours in Air at 250° C. | | |
|---|---|---|---|---|---|---|---|
| | | | | | 0 | 1.5 | 5 |
| XII[c] | 0.02 | Bis-α,α'(4-hydroxyphenylthio)-1,4-diisopropylbenzene (0.15 wt. percent) | 0.36 | 2 | .616 | .684 | .300 |
| XIII[b] | 0.02 | Bis-α,α'(4-hydroxyphenylthio)-1,4-diisopropylbenzene (0.15 wt. percent) | <0.4 | 2 | .677 | .436 | .310 |
| XIV[d] | 0.02 | Bis-α,α'(4-hydroxyphenylthio)-1,4-diisopropylbenzene (0.15 wt. percent) | 0.55 | 3 | .647 | .676 | .588 |
| XV[d] | 0.04 | Bis-α,α'(4-hydroxyphenylthio)-1,4-diisopropylbenzene (0.15 wt. percent) | 0.54 | 3 | .706 | .738 | .637 |
| XVI[d] | 0.08 | Bis-α,α'(4-hy- | 0.57 | 3 | .715 | .703 | .614 |

TABLE III-continued

| Example | P(TEDP) [Parts Per Thousand] | Antioxidant Stabilizer | I.V. at Addition of Stabilizer | Visual Color[a] Rating - 5 hrs at 250° C. | Intrinsic Viscosity Hours in Air at 250° C. | | |
|---|---|---|---|---|---|---|---|
| | | | | | 0 | 1.5 | 5 |
| XVII[d] | 0.04 | droxyphenylthio)-1,4-diisopropylbenzene (0.15 wt. percent) Bis-α,α'(4-hydroxyphenylthio)-1,4-diisopropylbenzene (0.15 wt. percent) | 0.54 | 3 | .660 | .686 | .638 |
| XVIII[d] | — | R5224 (0.15) | 0.55 | 3.0 | .625 | .663 | .625 |
| XVIX[d] | — | R5224 (0.30) | 0.55 | 3.5 | .650 | .685 | .640 |
| XX[de] | 0.04 | R5224 (0.15) | 0.60 | 3.5 | .711 | .695 | .670 |
| XXI[b] | 0.02 | None | — | 7 | .598 | .372 | .265 |
| XXII[b] | 0.02 | Irganox 1010 (0.15) | — | 6 | .564 | .647 | .559 |

[a]-The terephthalic acid based control polymer had a color rating of about 1.0 before the thermal testing: the higher the number the darker is the polymer color.
[b]-Both the P(TEDP) and the stabilizer were added before the condensation reaction had begun.
[c]-Both the P(TEDP) and the stabilizer were added when the polymer intrinsic viscosity was 0.36.
[d]-The P(TEDP) was added before the condensation reaction began.
[e]-R-5224 is the reaction product of 2-(1-phenethyl)-4-(phenethyl-1-thio) phenol with $PCl_3$ (10 percent of the theoretical amount). The final composition thus is essentially:

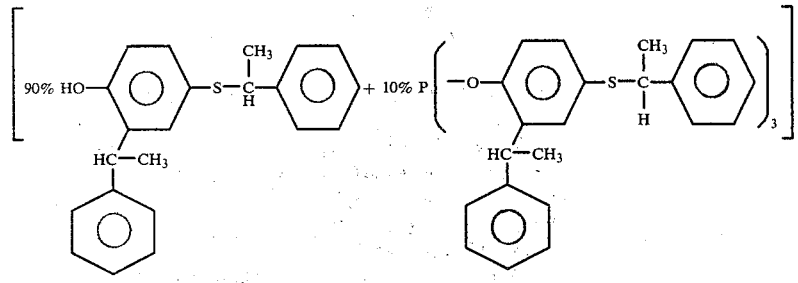

The data contained in Table III clearly indicate that the compounds of this invention are excellent stabilizers for polyesters. The compounds of this invention have both good color stability and tend to increase the molecular weight of the material it is intended to protect. However, Irganox 1010, presently the stabilizer of choice in the industry, does not provide good color stability.

EXAMPLE XXIII

Effect of Stabilizer in Absence of Phosphorus

A 54 gram sample of polyethylene terephthalate (I.V.=0.606) containing no phosphorus stabilizer was melted under vacuum at 275° C. A 6.5 gram sample of the melt was removed and set aside as an unstabilized control sample. To the remaining 47.5 grams of melted polymer was added 0.081 grams of bisα,α'(4-hydroxyphenylthio)-1,4-diisopropylbenzene stabilizer. This mixture was thoroughly stirred for a few minutes at atmospheric pressure. Vacuum was then applied for three minutes after which the system was restored to atmospheric pressure by the addition of nitrogen. A sample of this polymer containing stabilizer was removed for thermal stability tests. Samples of each of the above finely ground polymers were vacuum dried at 125° C. for 4 hours and then placed in a circulating air oven at 240° C. for various periods of time. Data is presented in Table IV.

TABLE IV

| Hours at 240° C. | Unstabilized Polymer-Control (Intrinsic Viscosity)* | Polymer Containing Mercaptophenol Derivative But No Phosphorus (I.V.)* |
|---|---|---|
| 0 | 0.736 | 0.749 |
| 1 | 0.303 | 0.826 |
| 3½ | 0.204 | 0.882 |
| 6½ | 0.188 | 0.853 |

TABLE IV-continued

| Hours at 240° C. | Unstabilized Polymer-Control (Intrinsic Viscosity)* | Polymer Containing Mercaptophenol Derivative But No Phosphorus (I.V.)* |
|---|---|---|
| **Visual Color at 6½ hr. | 10 | 3.0 |

*Intrinsic Viscosity measured in a 50/50 (by weight) mixture of dichloromethane and trifluoroacetic acid at a concentration of approximately 0.4 gram of polymer per $cm^3$ of solution.
**Control polymer had color rating of 1.0 before thermal testing: the higher the number the darker the color.

The data from Example XXIII indicate that use of compounds of formulae (I), (II) and (III) without a phosphorus stabilizer provides excellent color and thermal stability.

An unexpected facet of the present invention can be seen in Tables I to IV, that being the compounds of formulae (I), (II) and (III) increase the intrinsic viscosity of the polymer to which they are added. From the Tables it appears that compounds of the formulae (I), (II) and (III) increase the intrinsic viscosity of the polyester during the first 1 to 4 hours that it is heated in the hot air oven at from 240° To 250° C. This is an unexpected and highly desirable feature, in that thermal and color stability of a polyester can be achieved in conjunction with a high molecular weight polyester when compounds of formulae (I), (II) and (III) are employed.

INDUSTRIAL APPLICABILITY

The use of compounds of formulae (I), (II) and (III) will fulfill a long felt need in the polyester industry for stabilizers that greatly lessen the deleterious effects of thermal degradation and discoloration.

While certain representative embodiments and details have been shown for the purpose of illustrating the invention it will be apparent to those skilled in this art that various changes and modifications may be made therein without departing from the spirit or scope of the invention.

We claim:

1. A high molecular weight polyester having incorporated therein a stabilizing amount of a phenolic stabilizer selected from at least one of the following generic formulae (I), (II) and (III):

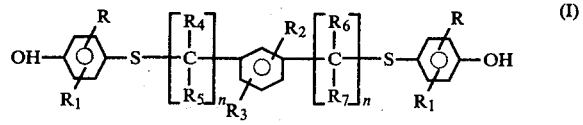

(I)

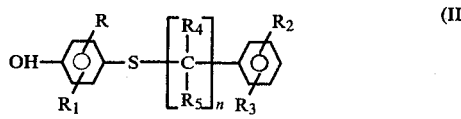

(II)

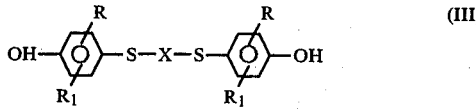

(III)

wherein R, $R_1$, $R_2$ and $R_3$ are the same or different radicals selected from the group consisting of hydrogen radical, alkyl radical of 1 to 18 carbon atoms, aralkyl radical of 7 to 24 carbon atoms; $R_4$, $R_5$, $R_6$ and $R_7$ are the same or different radicals selected from the group consisting of hydrogen radical, or alkyl radicals of 1 to 8 carbon atoms and n is 1 or 2; and X is selected from the group consisting of alkylene radicals of 2 to 18 carbon atoms, divalent cyclic radicals of 5 to 25 carbon atoms, divalent polycyclic radicals of 7 to 25 carbon atoms.

2. The polyester of claim 1 wherein the polyester is polyethylene terephthalate.

3. The polyester of claim 1 wherein 0.01 to 2.0 grams of said phenolic stabilizer is incorporated per 100 grams of the polyester.

4. The polyester of claim 1 wherein 0.05 to 1.0 grams of said phenolic stabilizer is incorporated per 100 grams of the polyester.

5. A high molecular weight polyester according to claim 1 wherein the phenolic stabilizer has the generic formula:

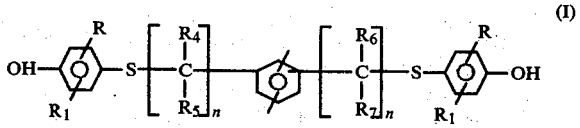

(I)

wherein R, $R_1$, $R_2$ and $R_3$ are the same or different radicals selected from the group consisting of hydrogen radical, alkyl radical of 1 to 18 carbon atoms, aralkyl radical of 7 to 24 carbon atoms; $R_4$, $R_5$, $R_6$ and $R_7$ are the same or different radicals selected from the group consisting of hydrogen radical, or alkyl radicals of 1 to 8 carbon atoms and n is 1 or 2.

6. A high molecular weight polyester according to claim 5 wherein at least one phenolic stabilizer is selected from the group consisting of:

Bis$\alpha,\alpha'$-(3,5-di-t-butyl-4-hydroxyphenylthio)-1,4-diisopropylbenzene;

Bis$\alpha,\alpha'$-(4-hydroxyphenylthio)-1,4-diisopropylbenzene;

$\alpha$-(4-hydroxyphenylthio)-$\alpha'$-(3,5-di-t-butyl-4-hydroxyphenylthio)-1,3-diisopropylbenzene;

Bis$\alpha,\alpha'$-(3-isopropyl-5-t-butyl-4-hydroxyphenylthio)-1,4-di-sec-butylbenzene; and 1,4-bis-[1-(4-hydroxyphenylthio)ethyl]benzene.

7. A high molecular weight polyester according to claim 1 wherein the phenolic stabilizer has the generic formula:

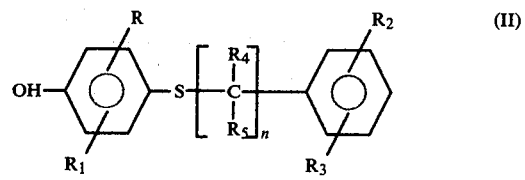

(II)

wherein R, $R_1$, $R_2$ and $R_3$ are the same or different radicals selected from the group consisting of hydrogen radical, alkyl radical of 1 to 18 carbon atoms, aralkyl radical of 7 to 24 carbon atoms; $R_4$ and $R_5$ are the same or different radicals selected from the group consisting of hydrogen radical, or alkyl radical of 1 to 8 carbon atoms and n is 1 or 2.

8. A polyester according to claim 7 wherein the phenolic stabilizer is:

2-(1-phenethyl)-4-(1-phenethyl-1-thio)phenol, and/or
2,6-bis-(1-phenethyl)-4-(1-phenethyl-1-thio)phenol.

9. A high molecular weight polyester according to claim 1 wherein the phenolic stabilizer has the generic formula:

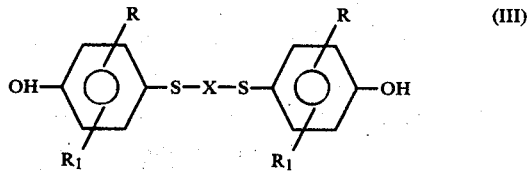

(III)

wherein R and $R_1$ are the same or different radicals selected from the group consisting of hydrogen radical, alkyl radical of 1 to 18 carbon atoms, aralkyl radical of 7 to 24 carbon atoms; and X is selected from the group consisting of alkylene radicals of 2 to 18 carbon atoms, divalent cyclic radicals of 5 to 25 carbon atoms, divalent polycyclic radicals of 7 to 25 carbon atoms.

10. A high molecular weight polyester according to claim 9 wherein at least one phenolic compound is selected from the group consisting of:

1,6-bis(3,5-di-t-butyl-4-hydroxyphenylthio)hexane;

5,11(12)-(4-hydroxyphenylthio)pentacyclo[8.2.$1^{4,7}0^{2,9}0^{3,8}$]-tetradecane; and 5,11(12)-3,5-di-t-butyl-(4-hydroxyphenylthio)pentacyclo[8.2.$1^{4,7}0^{2,9}0^{3,8}$]-tetradecane.

* * * * *

UNITED STATES PATENT AND TRADEMARK OFFICE
CERTIFICATE OF CORRECTION

PATENT NO. : 4,330,462
DATED : May 18, 1982
INVENTOR(S) : Keck et al

It is certified that error appears in the above-identified patent and that said Letters Patent is hereby corrected as shown below:

At Column 11 lines 52 and 55 delete:

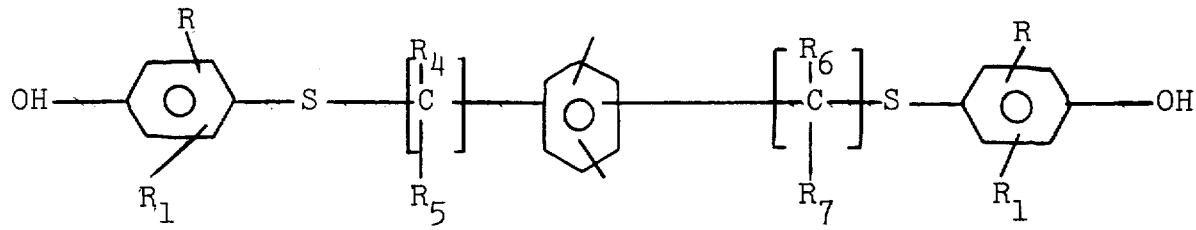

and insert therefor:

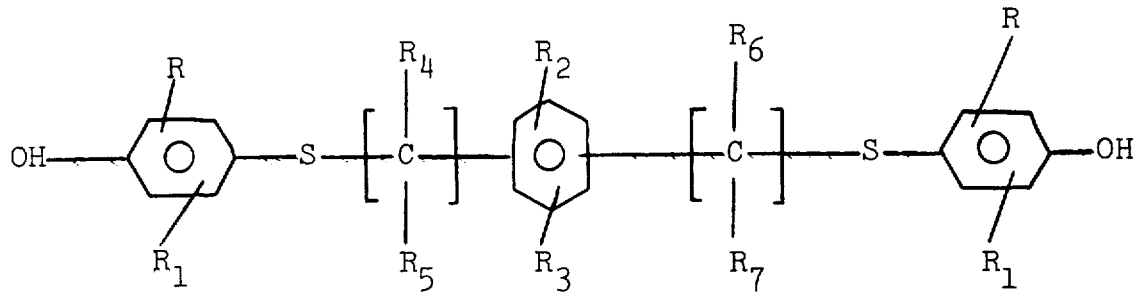

Signed and Sealed this

Tenth Day of June 1986

[SEAL]

Attest:

DONALD J. QUIGG

Attesting Officer    Commissioner of Patents and Trademarks